United States Patent [19]

Bender et al.

[11] Patent Number: 4,703,372
[45] Date of Patent: Oct. 27, 1987

[54] PORTABLE ELECTROCARDIOGRAPHIC RECORDER

[75] Inventors: Herman G. Bender, Hillsboro; Fred J. Shipley, Beaverton; Gary C. Vance, Portland, all of Oreg.

[73] Assignee: Spacelabs, Inc., Chatsworth, Calif.

[21] Appl. No.: 709,629

[22] Filed: Mar. 8, 1985

[51] Int. Cl.⁴ .............................................. G11B 5/008
[52] U.S. Cl. .................... 360/96.1; 360/96.6; 360/93; 360/105; 128/711; 226/187; 226/194
[58] Field of Search ..................... 360/96.6, 96.5, 96.4, 360/96.3, 96.1, 93, 105, 137; 128/711; 242/206, 207, 208; 226/186, 187, 190, 194

[56] References Cited

U.S. PATENT DOCUMENTS

| | | | |
|---|---|---|---|
| 3,684,295 | 8/1982 | Strain et al. | 360/96.5 X |
| 3,724,858 | 4/1973 | Martin | 360/96.1 |
| 3,849,799 | 11/1974 | Nakamichi | 360/96.6 |
| 3,893,186 | 7/1975 | Yoshii | 360/96.6 |
| 3,913,869 | 10/1975 | Richards | 242/206 |
| 3,932,892 | 1/1976 | Saito | 360/96.4 |
| 3,967,769 | 7/1976 | Matsumoto | 226/194 |
| 4,344,096 | 8/1982 | Tanaka et al. | 360/96.5 |
| 4,367,850 | 1/1983 | Moris | 360/93 X |
| 4,491,889 | 1/1985 | Tsuchiya | 360/96.6 X |
| 4,511,941 | 4/1985 | Ida | 360/93 X |

Primary Examiner—Robert S. Tupper
Assistant Examiner—Andrew L. Sniezek
Attorney, Agent, or Firm—Lawrence S. Levinson; Robert E. Lee, Jr.

[57] ABSTRACT

A portable recorder has a pinch roller moved to engage a capstan, a recording head brought into a recording position and a motor to power the recorder switched on through the sliding movement of a slide assembly in engagement with the case of the recorder near a hinge between bottom and top portions of the case. The capstan is rotated about an axis substantially perpendicular to the plane of the case by a pulley arrangement driven by the motor with an axis substantially within a plane parallel to the case. The recording head is mounted to the slide assembly which includes a roller attached to the back thereof for rotating engagement with the case when it is opened and closed. Rotating movement of the roller causes the slide assembly to move back and forth within the case as the top of the case is opened and closed causing the recording head to move near or away from the tape. A spring mounted to the case and the slide assembly biases the slide assembly to a remote position when the case is opened. A roller spring attached to the slide assembly engages the pinch roller biasing it into engagement with the capstan when the case is closed but a pawl member portion of the slide assembly is adapted to engage the pinch roller and move it away from the capstan when the case is opened. A roller spring disengagement mechanism is provided to keep the roller spring from engaging the pinch roller if the case is empty when closed.

7 Claims, 20 Drawing Figures

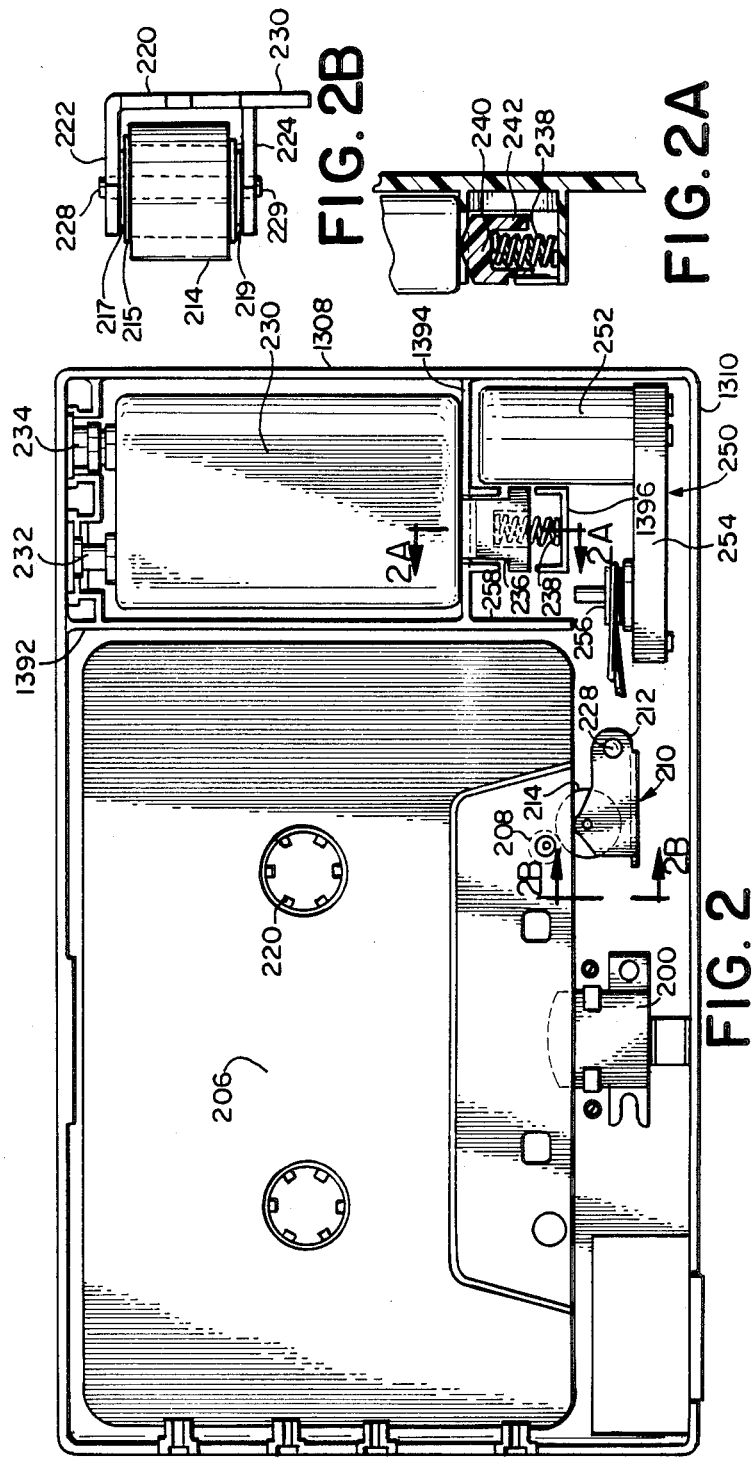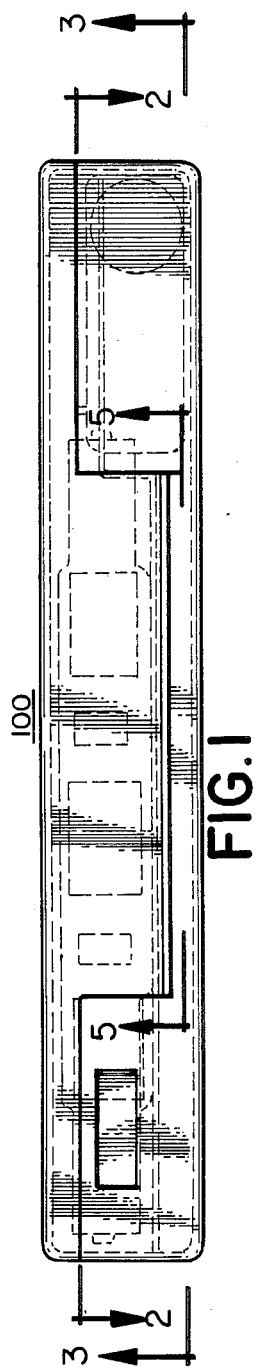

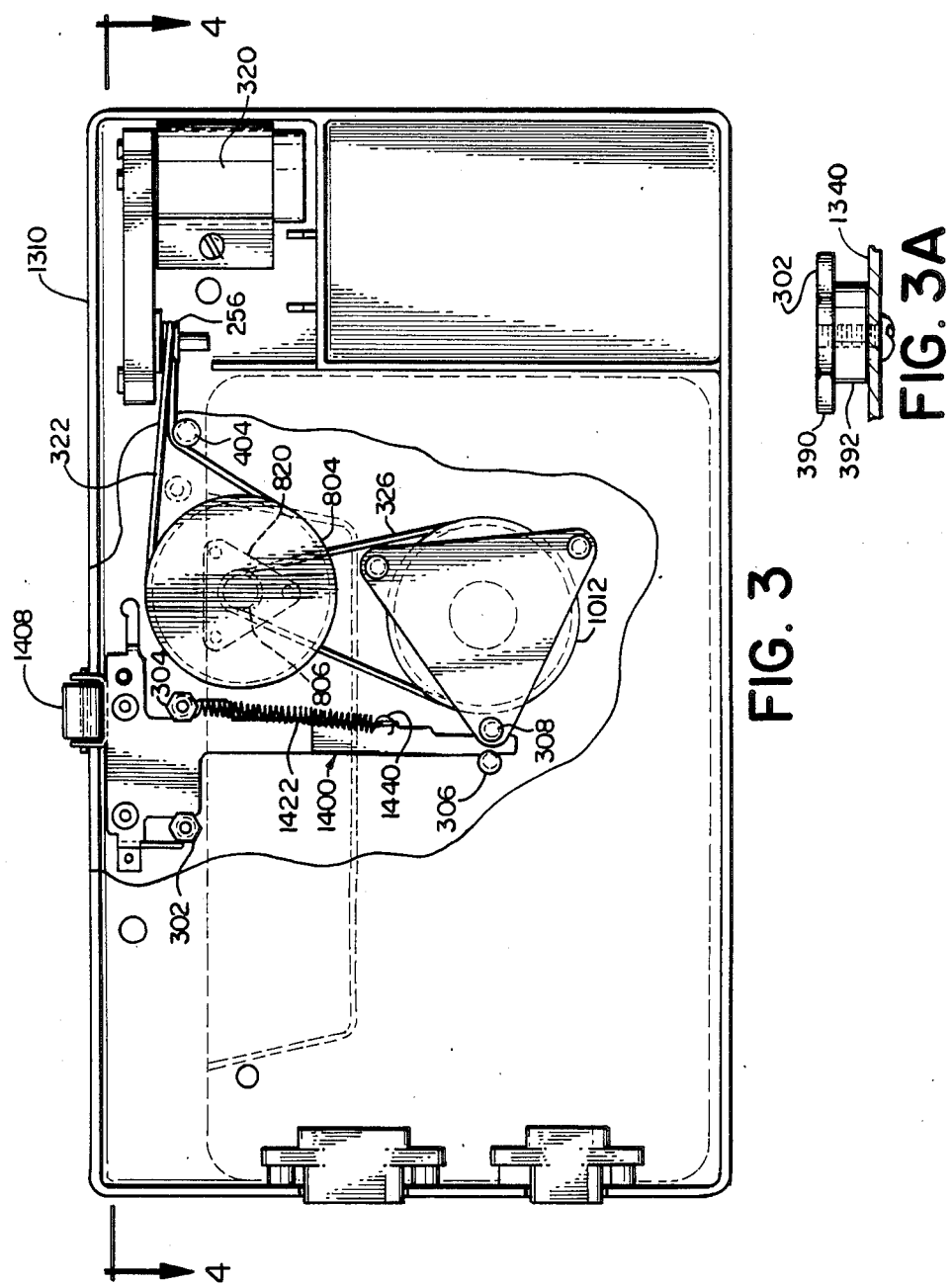

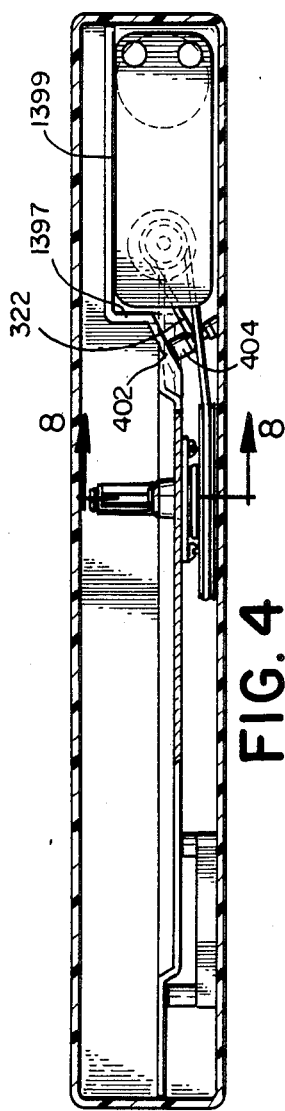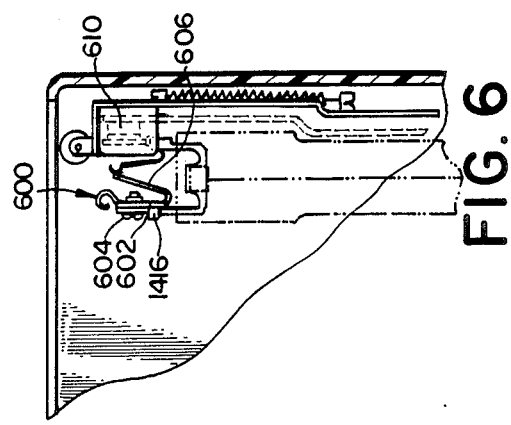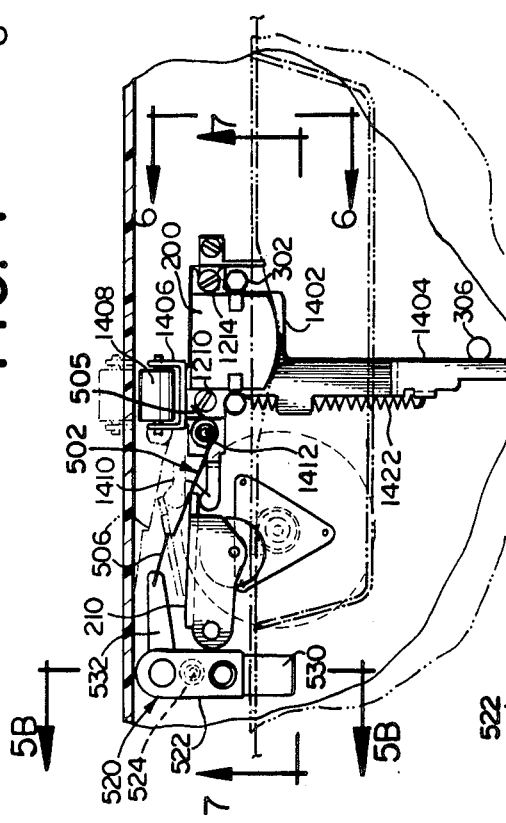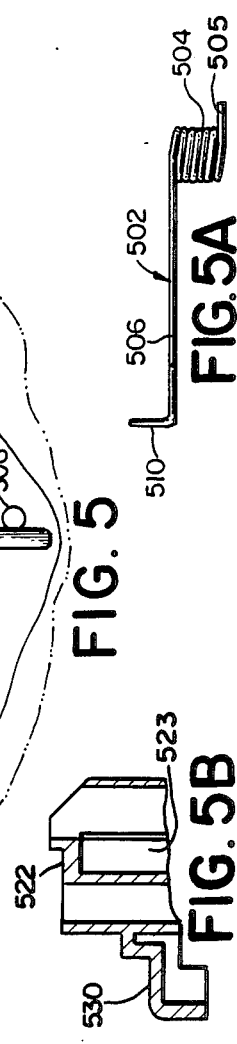

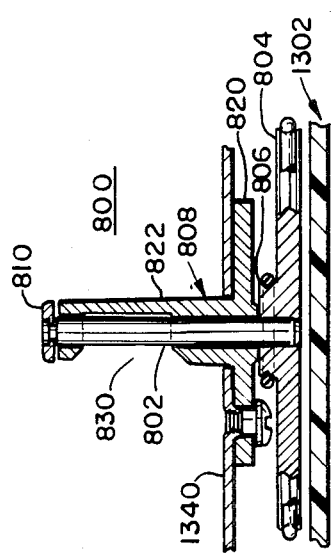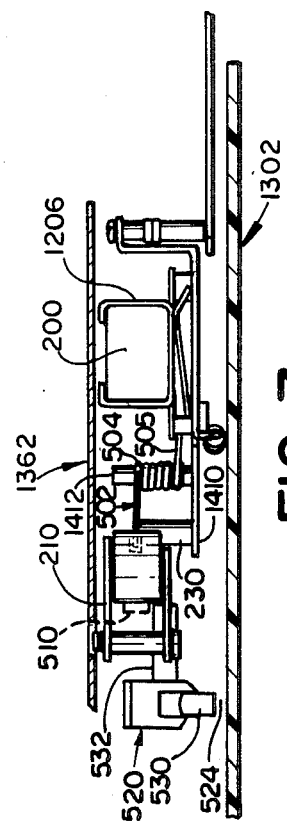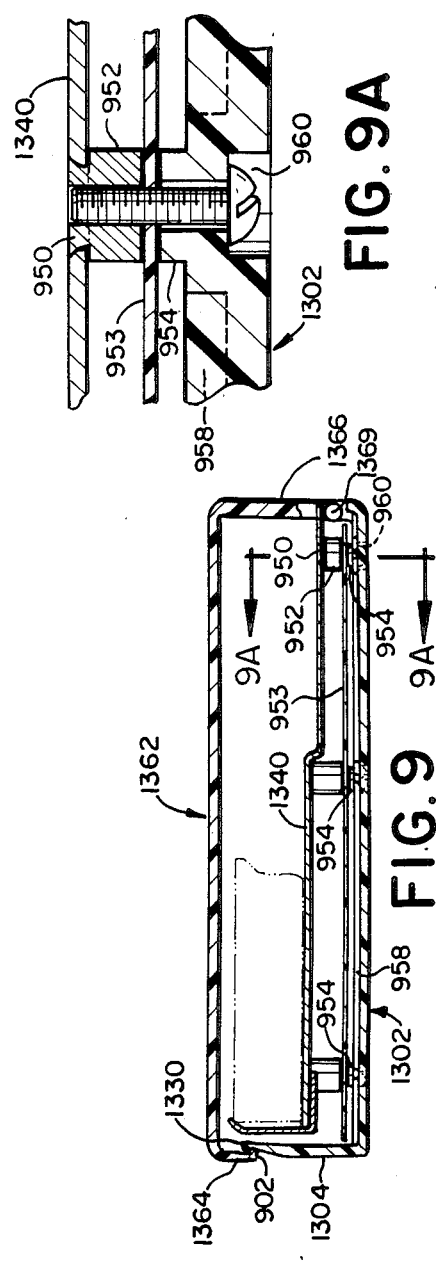

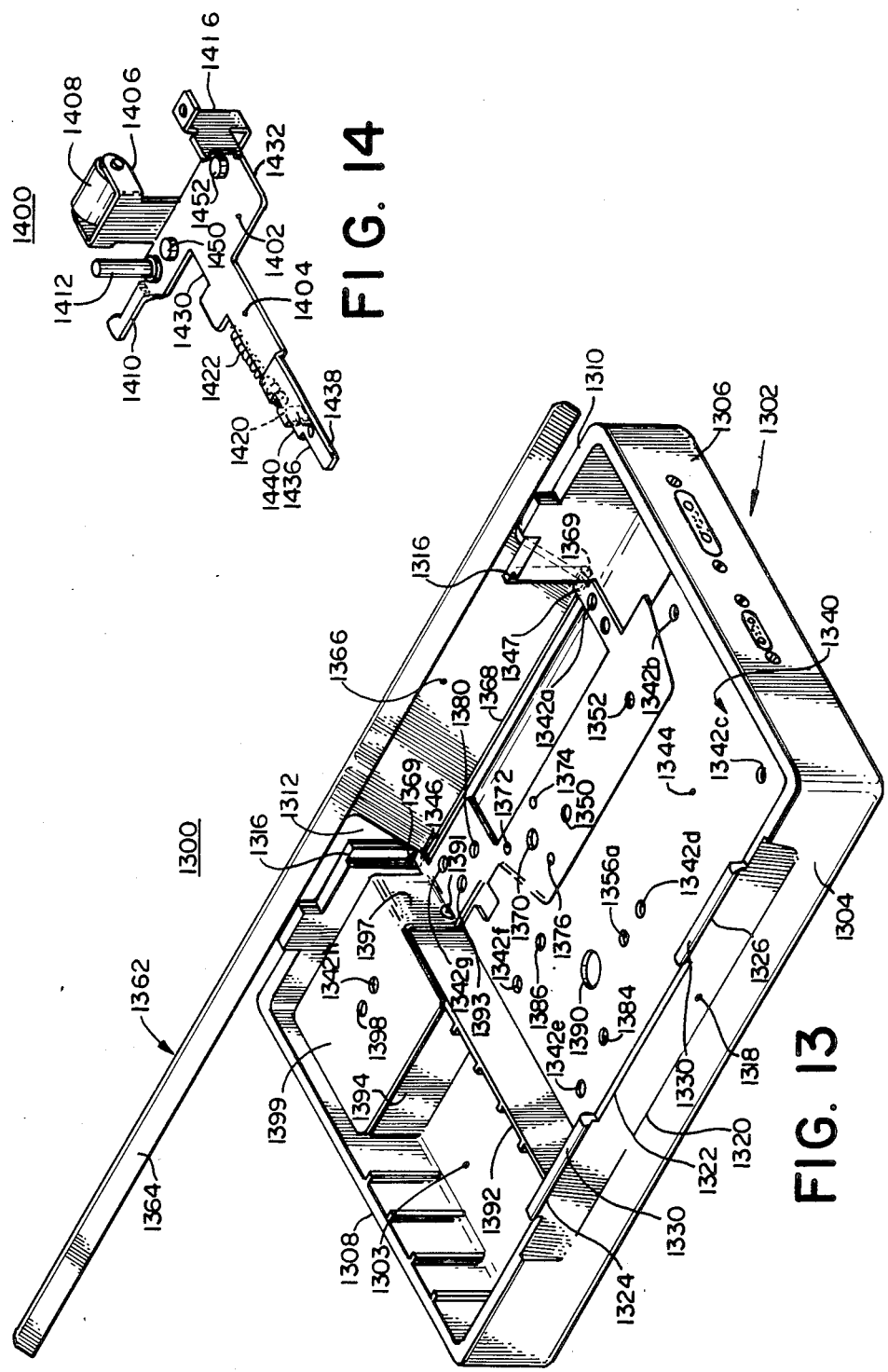

PORTABLE ELECTROCARDIOGRAPHIC RECORDER

BACKGROUND OF THE INVENTION

This invention relates to the recording of electrocardiographic signal recording and, more particularly, to an improved portable recorder.

Some forms of heart disorders during their early stages produce abnormal ECG's only infrequently and sporadically. To overcome this and detect heart disorders early, portable recorders in the prior art are worn by patients which recorders continuously record the patient's electrocardiographic (ECG) signals over an extended period of time while the patient engages in normal daily activities.

Those prior art recorders comprise a battery powered magnetic tape recorder mechanism which record on the standard size magnetic tape cassettes. With speeds of only one millimeter per second, the cassette is capable of recording anywhere from 24 to 48 hours worth of data.

Although relatively small and compact (6.1" by 3.9" by 1.6" and 1¾ to 2 lbs.), the prior art devices still represent a considerable nuisance to the wearer, and any reduction in size and weight would be a welcome improvement. However, the size and weight are controlled mainly by the size and weight of the battery, motor and cassette needed to record the 24 hours to 48 hours worth of data.

Further, in the prior art devices, while the case of the recorder is still open, the recorder head and pinch roller must be moved into recording position manually. When the case is closed a start switch is manually engaged. It is desireable to have all of this start automatically when the case is closed.

Further, in many prior art recorders an oil light bearing is used with the pinch roller and ball bearings with the capstan but because of the slow recording speed the oil light bearing is often inadequately lubricated causing premature failure and the indentations in the ball bearings introduce noise in the recordings.

SUMMARY OF THE INVENTION

The present invention provides for an improved, smaller, lighter, portable electrocardiographic signal recorder for use with ambulatory patients. The present invention recorder is only 5.5 by 3.3 by 0.8 inches and 9 oz. This small size is made possible through the use of several innovations.

The portable recorder includes a relatively planer case having a bottom and top movably mounted to the bottom, preferably hinged. A support means or frame is mounted inside the case, preferably to the bottom, for supporting a tape cassette on one side thereof. The recorder includes a capstan assembly including a rotatable capstan and a pinch roller assembly for cooperation with the capstan for moving the tape. The capstan is rotated about an axis substantially perpendicular to the plane of the case by a pulley arrangement driven by a motor and gear case assembly rotating about an axis substantially within a plane parallel to the case, the pulley arrangement including an idler pulley rotatable about an axis transverse to both the capstan and motor axis for rotating the belt coupling the gear case drive to the capstan.

The motor is automatically switched on, the pinch roller moved to engage the capstan, and a recording head brought into a recording position proximate the moving cassette tape when the top of the case is closed through the sliding movement of a slide assembly in engagement within the case near the hinge between the top and bottom.

The slide assembly comprises a body portion coupled to an elongated portion. The slide assembly is confined with the case by a roller attached to a back side of the body portion for rotating engagement with the case when it is opened and closed; a pair of retainers mounted to the bottom of the case in sliding engagement with opposite sides of the body portion and one retainer and a mounting post in sliding engagement with opposite sides of the elongated portion; and a spring attached to the elongated portion and to the case, preferably to one of the body side retainers.

A magnetic recording head is mounted on a top surface of the body portion of the slide assembly, and when the case is closed the top pushes against the roller forcing the slide assembly to move the recording head near to the tape against the action of the spring. When the case is opened, the spring contracts moving the slide assembly and recording head away from the tape. A roller spring attached to the slide assembly engages the pinch roller assembly biasing the pinch roller into engagement with the capstan when the case is closed but the slide assembly further comprises a pawl member adapted to engage the pinch roller assembly and move it from engagement with the capstan against the action of the spring when the case is opened.

Means are provided for disengaging the roller spring from the roller assembly if the case is empty to save wear on the pinch roller. Further, a plastic bearing is used to mount and support the rotating capstan. The plastic bearing is tough enough to wear over a long time with slow rotation of the capstan. The same plastic is used as a bearing for the roller and requires no oil lubrication like the oil light bearing.

BRIEF DESCRIPTION OF THE DRAWINGS

FIG. 1 is a front elevational view of the preferred embodiment recorder with the top of the recorder case in the closed position.

FIG. 2 is a top planer view of the inside of the bottom of the case showing the relative position of a portion of the components with respect to a tape cassette to be used with the recorder.

FIG. 2A is a partial cross section taken along the lines and arrows 2A—2A in FIG. 2.

FIG. 2B is an elevational view of a portion of the present invention taken along the lines and arrows 2B—2B in FIG. 2.

FIG. 3 is a planer view of the bottom of the recorder taken along the lines and arrows 3—3 in FIG. 1 with a portion of the bottom broken away to expose a portion of the components of the recorder.

FIG. 3A is an elevational view of a hex head retainer for use with the present invention.

FIG. 4 is a front elevational view of the recorder taken along the lines and arrows 4—4 in FIG. 3 and showing the mounting of the capstan assembly in more detail.

FIG. 5 is a top planer view of the recorder taken along the lines and arrows 5—5 in FIG. 1 with a portion broken away to show the cooperation of several of the components of the recorder.

FIG. 5A is a side view of the roller spring of FIG. 5 attached to the slide assembly.

FIG. 5B is a cross-sectional view of the mechanism 520 taken along the lines and arrows 5B in FIG. 5.

FIG. 6 is a side elevational view taken along the lines and arrows 6—6 in FIG. 5.

FIG. 7 is a front elevational view taken along the lines and arrows 7—7 in FIG. 5.

FIG. 8 is a cross sectional view of the capstan assembly of FIG. 4 taken along the lines and arrows 8—8.

FIG. 9 is a side cross sectional view of the case and an internal frame of the recorder of FIG. 1.

FIG. 9A is a cross sectional view of a portion of the recorder taken along the lines and arrows 9A—9A in FIG. 9.

FIG. 13 is a perspective view of the case of the recorder with the top open and showing only the internal frame mounted inside.

FIG. 14 is a perspective view of a slide assembly portion of the preferred embodiment recorder.

DETAILED DESCRIPTION OF THE INVENTION

1. Description of Case and Frame

Figure 10:
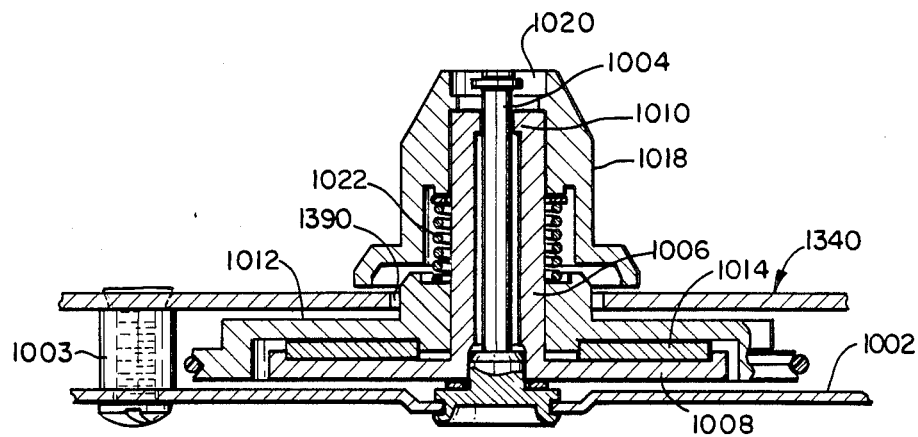
FIG. 10 is a detailed cross sectional view of a take up spindle portion of the recorder of FIG. 1.

Referring first to FIG. 13, the FIG. shows a perspective view of the case designated generally 1300 of the preferred embodiment recorder (designated generally 100 in FIG. 1) with the top of the case shown partially open. The case is made of molded plastic and relatively thin in height compared to the thickness of the standard 9V battery, or standard cassette tape which it is required to accommodate, and substantially planer in design.

The case comprises a bottom member designated generally 1302 having a bottom 1303, a front wall 1304, side walls 1306 and 1308 and back wall 1310 with a cut out in wall 1310 in the region 1312 which is at least one half of the height of the wall 1310 itself. The walls have a certain thickness, with front and back walls 1304 and 1310 being slightly thicker than side walls 1306 and 1308.

Back wall 1310 includes a slot 1316 on opposing edges of the back wall forming the cut out in region 1312. Further, the front wall contains a region of indentation 1318 which is tapered in thickness from full wall thickness at line 1320 to approximately half wall thickness at the top of the wall at 1322. Two tabs 1324 and 1326 are connected to the top of the front wall 1304 in the indentation region. The tabs have a taper or laterally extending portion 1330.

The recorder further comprises a frame designated generally 1340. Frame 1340 is adapted for attachment to the bottom of the case by internally threaded posts which are staked into the bottom of the frame at locations 1342 a-h. Each post (an example of one is shown in cross section in FIG. 9A) has a portion 950 staked into the frame 1340 and an enlarged cylindrical portion 952 extending away from the bottom of the frame. Each post rests on a circuit board 953 which is supported on raised portion 954 of plastic ribs (such as rib 958) located on the floor of the bottom of the case and molded integrally therewith. Holes (such as hole 960) are provided through the bottom of the case, the circuit board 953 and the raised portions at several locations. Screws inserted from the bottom up are screwed into the posts to secure the frame to the bottom sandwiching the circuit board inbetween.

The frame comprises a substantially planer portion 1344 for supporting a tape cassette for recording the ECG information. The frame is also used for supporting various other components.

Circuits for operating the head and recording the ECG information are well known and form no part of the present invention. The circuit components are mounted to the circuit board using a surface mounting technique. However, the overall packaging of the recorder components including the relative mounting of the circuit board with surface mounted components is one aspect of the present invention.

The top member designated generally 1362 of the recorder case is a substantially planer molded plastic part having a top surface and integrally molded side, front and back walls 1364 which are generally much smaller in height than the walls of the bottom member except in the region 1312 of the cut out in the back wall 1310. There the top has downwardly extending wall portion 1366 with hinge portion 1368 along the bottom edge thereof. The hinge portion comprises outwardly extending cylindrical portions 1369 at the ends thereof which are adapted to fit within slots 1316.

The frame 1340 further comprises tabs 1346 and 1347 which extend to cover of the cylindrical portions 1369 and thereby pivotably connect the top member 1362 to the bottom member 1302.

Referring to FIG. 9, a cross section of the case in the closed positioned with the frame in place is shown. The top member 1362 comprises an inwardly extending lip 902 along a portion of the edge of the front wall 1364 of the top member in the region of the tabs 1324 and 1326. These tabs, made of plastic and being relatively thin, are resiliently deflectable such that when the edge of the front wall 1364 engages them they deflect inwardly allowing the lip 902 to snap into place under extending portions 1330, thereby locking the case shut.

Unlike prior art devices the present invention is designed to provide automatic record and power off features activated by the opening and closing of the case. With the present invention when a patient is fitted with a device, a cassette is placed inside and the case closed. The power is turned on, the tape begins to move, and the recording begins. When the case is opened after the recorder is removed from the patient everything automatically stops.

This is brought about by the cooperation of several different assemblies which are mounted inside the case including: a slide assembly for moving in and out with the closing and opening of the case; a recording head and mounting assembly for mounting the recording head on the slide assembly; a capstan assembly and pinch roller assembly for moving the tape in the cassette across the recording head; a take up spindle for use with the cassette; and a motor, gear case and pulley arrangement for applying a drive to the capstan and take up spindle. Other components include a pawl member and biasing spring attached to the slide assembly for automatically engaging and disengaging the pinch roller with regard to the capstan with the opening and closing of the case and an assembly for disabling the pinch roller biasing spring when the case is closed without a cassette inside. An automatic motor switch assembly is provided which is activated by movement of the slide assembly and a special plastic bearing design for the capstan and pinch roller is provided to minimize wear and prolong the life of the bearing.

2. Description of the Slide Assembly and Frame Mounting Thereof

FIG. 14 is a perspective view of the slide assembly designated generally 1400. It comprises a substantially planer body portion 1402 and an elongated portion 1404 coupled thereto and formed integrally therewith. A roller holder 1406 for pivotably holding a roller 1408 is connected to the back side of the body portion 1402. It extends vertically upward from the body portion.

The slide assembly further comprises a first pawl member 1410 attached to one side of the body portion 1402 and extending outwardly therefrom. A vertical post 1412 is staked to the body portion near where the pawl member 1410 is attached.

A compound bracket 1416 is attached to the side of the body portion 1402 opposite the first pawl member, while a second pawl member 1420, shown dotted, is attached to the elongated member 1404 and extends vertically downward.

Referring to the FIGS., the slide assembly is confined within the case by steel hex head retainers 302 and 304 screwed to the frame from the bottom at locations 1350 and 1352; by a post 306 staked into the frame at location 1342d and by a take up spindle mounting post 308 staked into the frame at location 1356a. The retainers have the shape in FIG. 3A comprising a hex head 390 and the cylindrical body 392.

The sides 1430 and 1432 of slide assembly 1400 slide between the body portions 392 of the retainers 302 and 304 while the sides 1436 and 1438 slide between the posts 306 and 308. The hex heads of the retainers 302 and 304 overlap the body portion 1402 while the frame mounting post 306 has portion which overlaps the elongated portion 1404. The overlaps keep the slide assembly in a horizontal plane.

The biasing spring 1422 is connected at end 1440 to a notch in second pawl member 1420 and at its other end to the retainer 304. In FIG. 3 the roller 1408 is shown in a remote position extending beyond the back wall 1310 of the bottom of the case in the region 1312 which is the position the roller is in due to the aotion of the spring 1422 when the top of the case is opened. However, when the top member of the case is brought to the closed position the inside surface of top wall portion 1366 engages the roller 1408 pushing the slide assembly 1400 into the case against the biasing action of the slide spring 1422. When the case is fully closed, the slide assembly is in the record position (shown in FIG. 5). The slide assembly is comfined by the retainers, posts, spring 1422 and wall portion 1366.

3. Recording Head and Mounting Assembly

Figure 11:
FIG. 11 is a bottom view of the recording head mounting bracket and leaf spring.
Figure 12:
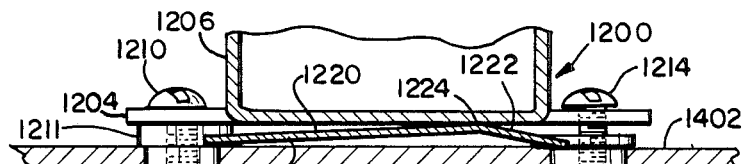
FIG. 12 is an elevational cross sectional view of the bracket of FIG. 11 shown mounted to a portion of a slide assembly along with the leaf spring for head adjustment.

The preferred embodiment recorder uses a four track, four channel cassette analog magnetic tape head made by VICRON, Inc., chosen from VICRON's P-3Q1-B7 family of recorder heads (and slightly modified) for recording the ECG information on the cassette tape. The recording head is part of the recording head assembly which is attached to the slide assembly 1400 at the hole locations 1450 and 1452 in base portion 1402. The recording assembly comprises the above mentioned recording head 200 shown in FIG. 5 attached to the slide assembly and in FIG. 2 without the slide assembly but shown in relative position to the cassette tape 206 in the recording position. The recording assembly further comprises in FIGS. 11 and 12 the mounting bracket 1200 and adjustment spring 1202.

The mounting bracket comprises the straight base plate 1204 and U-channel clamp 1206. The base plate 1204 is screwed down tight by screw 1210 to a slotted post 1211 staked into the base portion 1402 of slide assembly 1400 at hole 1450. At the opposite end of base plate 1204 there is located a slot 1100 through which a screw 1214 is inserted and screwed into a post staked into hole 1452. Adjustment spring 1202 is positioned between the bottom of base plate 1204 and the top surface of base portion 1402. Adjustment spring 1202 forms an angle with its unequal sides 1220 and 1222 and the apex 1224 of the angle engages the base plate biasing the mounting bracket away from the slide assembly forcing the recording head upward. The height of the recording head above the slide assembly can therefore be controlled by tightening or loosening the screw 1214. The slot 1100 aids in this adjustment by allowing the mounting bracket to move slightly laterally relative to screw hole 1452 with tightening or loosening of the screw 1214.

The tape is moved within the cassette past the recording head by the capstan assembly, pinch roller assembly and take up spindle. These will be described in more detail in that order below.

4. Capstan Assembly

The capstan assembly designated generally 800 is best seen in cross sectional detail in FIG. 8. It comprises a polished stainless steel capstan 802, a double pulley 804 (larger) and 806 attached as one piece to the bottom of the capstan by press fit, a bearing 808 for rotatably mounting the capstan to the bottom of the frame 1340 and a polyurethane retainer 810.

The bearing is a molded plastic part preferably made of an acetyl compound with the product name DELRIN 100 AF. It comprises a triangularly shaped base 820 and hollow cylindrical portion 822 perpendicular to the base 820 and integrally molded therewith. A portion of the wall of the cylindrical portion is absent forming a notch or opening 830.

During assembly the capstan 820 and cylindrical portion 822 are inserted from the bottom through hole 1370 in frame 1340 with the opening 830 generally facing toward the back wall of the bottom of the case. The bearing is screwed to the bottom of the frame at hole locations 1372, 1374 and 1376. Then the retainer 810 is snapped onto a slot in the top of the capstan. This secures the capstan assembly 800 including the pulleys 804 and 806 to the frame 1340.

5. Pinch Roller Assembly

Referring to FIG. 2, when the cassette 206 is positioned in the case (in FIG. 2 the top is shown removed) the capstan is positioned through a hole 208 in the cassette behind the tape of the cassette which is stretched across the front of the cassette. A pinch roller assembly 210 comprises a U shaped bracket 212 and rotatable roller 214 and is positioned such that the roller 214 pinches the tape against the capstan when the case is closed and the recording head 200 is in the record position.

FIG. 2B shows a side view of the shape of the bracket 212 comprising a base 220 and parallel arms 222 and 224.

The roller 214 is molded rubber which is slipped onto a cylindrical plastic bearing 215 (made from DELRIN 100 AF). The bearing is pinned onto the bracket at 228 and 229 in FIG. 2B. The bearing further comprises surfaces 217 and 219 which engage the inside surfaces of arms 222 and 224 as the roller and bearing rotate. The plastic bearing requires no lubrication and has characteristics which provide extended life for slow rotations. In prior art devices an oil light bearing is used which because of the slow rotation is often inadequately lubricated. The roller assembly 210 is pivotably mounted by a post through hole 228 in the bracket staked to the top of the frame at hole 1380. The base 220 of the bracket has a portion 230 which extends past arm 224 downwardly into the bottom of the case, the purpose of which will be described hereinafter.

6. Take-Up Spindle

A take up spindle designated generally 1000 is described in detail in cross section in FIG. 100 and cooperates with the capstan and pinch roller to move the tape. The take-up spindle is fairly conventional in design for a cassette recorder comprising: a triangular plate 1002 which is mounted by posts (such as post 1003) staked to the underside of frame 1340 at hole locations 1384, 1386 and 1356a; a shaft 1004 to which at the bottom the plate 1002 is coupled; a spindle drive 1006 having a bottom circumferential plate member 1008 engaging the bottom of the shaft 1004 and an elongated cylindrical member 1010 formed integrally with the bottom and engaging the shaft near its top; a pulley 1012 coupled to the drive 1006 by clutch pad 1014; and a hub 1018 engaging the outer circumference of a top portion of cylindrical member 1010. The hub is fixed in place by retainer clip 1020 at the top of shaft 1004 and by compression spring 1022 positioned around portion 1010 between a bottom portion of hub 1018 and a top surface of pulley 1012. The shaft 1004 and member 1010 extend upward through hole 1390 of frame 1340. Hub 1018 extends into a geared opening 220 in a reel within cassette 206 when the cassette is in place. As the capstan and pinch roller move the tape the take up spindle moves the reels within the cassette to store the tape through the action of the pulley and clutch.

7. Motor, Gear Case and Pulley Arrangement

The portable recorder of the present invention uses a conventional 9 V alkaline battery 230 for a portable power source. As best seen in FIGS. 2 and 2A the battery fits in the plane of the case within a compartment in the bottom of the case formed by molded walls 1392 and 1394 and side wall 1308 adjacent a side of the cassette 206 and separated therefrom by wall 1392. When the battery is placed in the compartment its terminals come in contact with mating terminals 232 and 234 attached to the front wall of the bottom of the case.

The battery terminals are biased against terminals 232 and 234 by the battery slide 236 and spring 238 and wall. Battery slide 236 has an angular portion 240 and a hollow circumferential portion 242 extending therefrom. The apex of the angular portion is designed to engage the bottom of the battery 230 through an opening in wall 1394. The spring is positioned within the cylindrical portion 242 and engages at one end a molded wall 1396 spaced apart from the opening in the wall 1394 such that the spring biases the slide to push the battery against the terminals 232 and 234.

The drive for the cassette assembly and take-up spindle assembly pulleys is provided by the motor and gear assembly designated generally 250 in FIG. 2. The motor and gear assembly comprises a motor 252 with a drive axis in the plane of the case parallel with wall 1308 and a gear case 254 for rotating a pulley 256 about an axis parallel with the drive axis of the motor 252 in the plane of the case. The motor and gear assembly are located in a compartment of the case formed by a portion of side wall 1308, a portion of back wall 1310 and an extension 258 of wall 1392.

The preferred embodiment uses a Namiki Model No. 12CL2010 motor and Namiki Model No. LG12C gear case. Other motors and gear cases with different speeds and speed reduction can be used.

The motor and gear assembly is attached by clamp 320 in FIG. 3 to hole 1398 of a raised portion 1399 of frame 1340 seen in FIG. 13. The raised portion 1399 is attached to the bottom of the case via a post and screw at location 1342h and is partially supported by wall 1394. It is coupled to the substantially planer portion 1344 by a vertical portion 1397 which has an inclined portion 402 at the junction between the vertical portion 1397 and substantially planer portion 1344, best seen in FIG. 4.

The inclined portion 402 supports an intermediate idler pulley 404 (at location 1391 in FIG. 13) whose axis is transverse to both the axis of the gear case pulley 256 and the axis of the capstan 802. As best seen in FIG. 3, the main pulley belt 322 comes off the gear case pulley 256 at the bottom and couples directly to the pulley 804 of the capstan assembly. The belt 322 wraps around the pulley 804 more than 180° but less than 270° and engages the idler pulley 404 on a side facing toward the back of the case as opposed to the front whereupon the pulley belt 322 wraps around the gear case pulley 256 on its top. Hence, the idler pulley 404 serves to rotate the belt 322 so that the drive for the gear case pulley 256 is transmitted to the capstan pulley 804 whose axis of rotation is perpendicular to the axis of the gear case pulley.

The drive of the capstan pulley 804 is transmitted to the take up spindle pulley 1012 by a second belt 326 coupled around the smaller capstan pulley 806 and the take-up spindle pulley 1012.

8. Automatic On-Off Switching Arrangement

As mentioned earlier, the preferred embodiment recorder is automatically turned on to the recording mode when the case top is closed and automatically turned off when it is opened. To accomplish this, the power from the battery must be coupled on and off to the motor. This is done through action of the slide assembly which comprises a switch spring 600 mounted to bracket 1416. As best seen in FIG. 6, the spring 600 comprises a horizontal portion 602 screwed to bracket 1416 by screw 604, and a diagonal portion 606 which extends generally downwardly. As the slide assembly moves from the remote position to the record position, the diagonal portion activates microswitch 610 attached to circuit board in the corner region of the bottom of the case formed by side and back walls 1306 and 1310, respectively. The microswitch 610 is electrically coupled partially by way of the circuit board to the motor and to the battery terminals. (The battery terminals, motor, and recorder head are coupled by wires to the circuit board.)

9. Slide Assembly Pawl and Roller Spring Arrangement

Referring now to FIGS 5, 5A, 5B and 7 the record position of the slide assembly, recording head and pinch roller is shown in solid line while their remote position is shown dotted. The recorder comprises a roller spring 502 which has one end 504 coiled around the slide assembly post 1412 and a short portion 505 extending therefrom to engage post 1211. The rest of the spring comprises a generally straight section 506. The end of straight section 506 is bent at 90° to form an extension 510 to the straight section directed upwardly from the bottom of the case (see FIG. 7).

The spring is disposed to engage the back of the pinch roller mounting bracket 210 biasing it such that the roller comes into contact with the tape and presses it against the capstan through through the opening 830 in the bearing 808.

When the case is opened the slide assembly 1400 moves to the dotted remote position in FIG. 5 because of the action of spring 1422 and the slide assembly pawl member 1410 engages the inside edge of the extended portion 230 of the roller bracket causing the roller to move away from the capstan assembly.

The recorder assembly further comprises an automatic roller spring disengagement mechanism designated generally 520 shown in longitudinal cross section in FIG. 5B. It comprises a main body 522 which is movably attached by posts staked to holes 1342g and 1393 of the frame 1340. The main body comprises a cylindrical hollow region 523 in which a spring 524 shown dotted in FIG. 5 is positioned to bias the mechanism for movement vertically upward from the floor of the bottom of the case.

The mechanism further comprises a first pawl member 530 extending laterally from the body 522 away form the back wall of the case, and a second pawl member 532 extending laterally from the body 522 in a direction generally toward the slide assembly adjacent the base wall.

The first pawl 530 member is disposed such that when a cassette is present in the case, whether the case is open or closed, the cassette engages the first pawl member 530 moving the mechanism 520 downward. When the case is opened, the pawl member 1410 moves the roller assembly and roller spring to the dotted position, and when the cassette is removed the mechanism 520 moves upwardly due to the spring 524. This places the second pawl member 532 between the upwardly extending portion 510 of the roller spring and the pinch roller assemblly (see FIG. 7 where mechanism 520 is shown in the depressed position). If the case is closed without a cassette positioned therein, the motor will automatically drive the capstan but the pinch roller will not engage the capstan. This saves wear on the roller and roller bearing.

If a cassette is placed in the case before closing, it engages the first pawl member 530 lowering the mechanism and moving the second pawl member 532 out of the way. The action of the slide assembly 1400, pawl members 1410, 530 and 532, the roller spring 502 and the mechanism 520 cooperate to automatically engage and disengage the pinch roller and capstan and prolong the lifetime of the roller and capstan bearings when a cassette is not present in the case.

FIG. 7 is a frontal view of the arrangement of the slide assembly 1400, recording head assembly (head 200 and bracket 1206), pinch roller assembly (bracket 210 and roller 214) and, disengagement mechanism 520 roller spring 502.

What is claimed is:

1. A portable apparatus for recording electrocardiographic signals on a tape of a cassette over an extended playing period, said apparatus comprising:

a relatively planer case having a bottom and a top movably mounted to said bottom between an open and closed position;

a support means mounted to said case for supporting said cassette in said case;

a power source terminal contained within said case for coupling to a portable power source;

means for moving said tape within said cassette in response to power from said terminal, said moving means further comprising a capstan and movable pinch roller for driving said tape;

a recording means for recording ECG information on said tape, said recording means automatically movable between a remote non-recording position and a recording position proximate said moving tape with the opening and closing, respectively, of the top of said case, said recording means further comprising:

a recording head;

a slide assembly slidably mounted to said support means for supporting said recording head, said slide assembly further comprising:

a main body portion and elongated portion connected to said body portion;

a roller support coupled to a first side of said body portion adjacent the top and bottom of said case where said top is movably mounted to said bottom, said roller support for supporting a roller for rotating engagement with said case as the top of said case is closed;

a pawl member and roller spring coupled to said body portion and engaging said pinch roller for biasing said pinch roller against said tape and capstan when the case is in the closed position and for moving said pinch roller away from said tape and capstan when said recorder is in the open position, said apparatus further comprising:

means movable along an axis between a depressed position and a biased position for preventing said roller spring from biasing said pinch roller against said capstan when said case is empty, said means comprising:

first biasing means for biasing said preventing means to said biased position;

a first pawl member disposed for engagement with said cassette when said cassette is positioned in said case to maintain said preventing means in said depressed position; and a second pawl member disposed for placement between said roller spring and said pinch roller when said case is open and empty of said cassette, whereby when said case is closed without a cassette said roller spring is prevented from engaging said pinch roller.

2. The apparatus of claim 1 wherein said moving means further comprises:

a motor means;

a gear case for reducing the speed of said motor means and rotating a pulley of a preselected first size around an axis parallel with the axis of said motor means and in a plane substantially parallel with the plane of said case;

an idler pulley rotatable about an axis transverse to said gear case pulley, and said apparatus further comprising:

a pulley attached to said capstan and rotatable about an axis substantially perpendicular to said planer case, said idler pulley serving to partially rotate a pulley belt coupled to both said gear case and capstan pulleys whereby the drive of said motor means is coupled to said capstan.

3. The apparatus of claim 1 wherein said recoring means further comprises:
   a mounting means for adjustably mounting said recording head to said slide assembly for alignment with said cassette.

4. The apparatus of claim 3 wherein said mounting means comprises:
   a bracket for receiving said recording head, said bracket adapted to be fixedly attached to said slide assembly at one end and variably attached at an opposite end; and
   an adjustment spring positioned intermediate the bottom of said bracket and said slide assembly for biasing said bracket against said attachments.

5. The apparatus of claim 1, wherein said apparatus further oomprises:
   a plurality of retainers attached to the bottom of said support means with at least one of said retainers in sliding engagement with opposite sides of said body portion and at least one retainer in sliding engagement with a side of said elongated portion.

6. The apparatus of claim 1 wherein said slide assembly further comprises:
   a second biasing means coupled to said elongated portion at one end and to the bottom of said case at the other end for biasing said roller in rotating engagement with said case.

7. The apparatus of claim 6 wherein said second biasing means is a coiled spring attached to one of said retainers on either side of said body portion of said slide assembly.

* * * * *